United States Patent
Summers

[11] 3,952,746
[45] Apr. 27, 1976

[54] HUMIDITY INDICATING DIAPER COVER

[76] Inventor: F. Wayne Summers, 256 Craigmeade Drive, Nashville, Tenn. 37214

[22] Filed: July 29, 1974

[21] Appl. No.: 492,686

[52] U.S. Cl. ............................ 128/287; 128/284; 128/290 R; 116/114 AM
[51] Int. Cl.² ........................................ A61F 13/16
[58] Field of Search ............... 128/284, 287, 290 R, 128/296; 116/114 AM

[56] References Cited
UNITED STATES PATENTS

| | | | |
|---|---|---|---|
| 1,843,234 | 2/1932 | Karnes et al. | 116/114 AM |
| 2,918,893 | 12/1959 | Norton | 116/114 AM |
| 3,004,895 | 10/1961 | Schwartz | 128/290 R |
| 3,084,658 | 4/1963 | Schell | 116/114 AM |
| 3,198,163 | 8/1965 | Williams | 116/114 AM |
| 3,731,685 | 5/1973 | Eidus | 128/284 |

*Primary Examiner*—Aldrich F. Medbery
*Attorney, Agent, or Firm*—Harrington A. Lackey

[57] ABSTRACT

A humidity indicator for a diaper including a moisture impervious outer sheet and a moisture absorbent inner sheet. A transparent opening is formed in the outer sheet either for viewing a moisture indicator strip behind the outer sheet or for exposing the moisture indicator strip on the outside of the outer sheet to communication with the moisture in the absorbent inner sheet.

7 Claims, 13 Drawing Figures

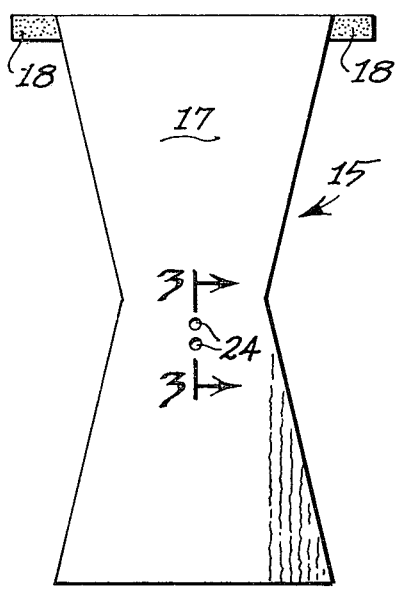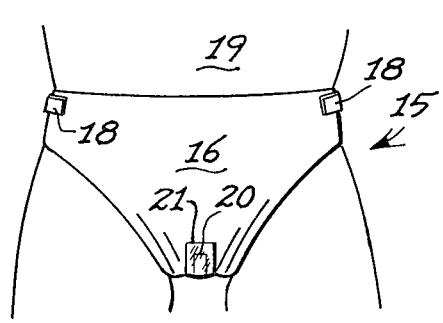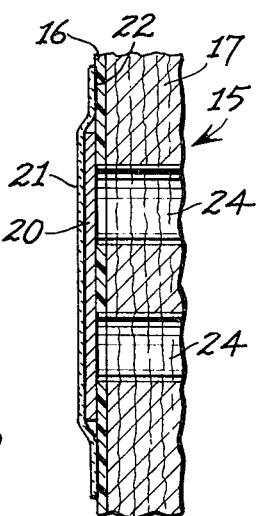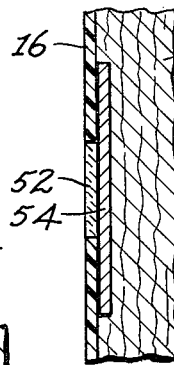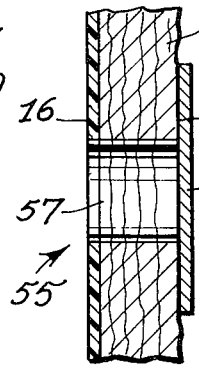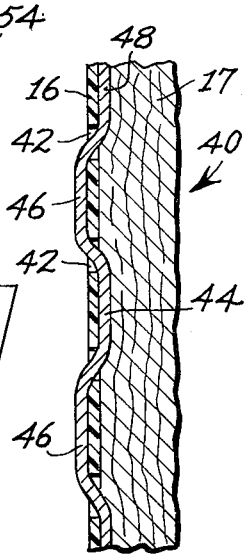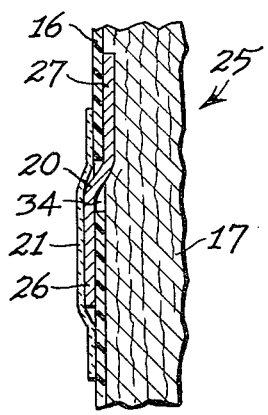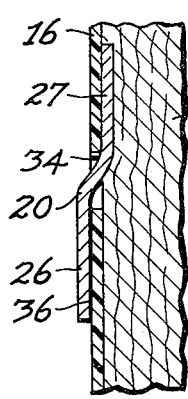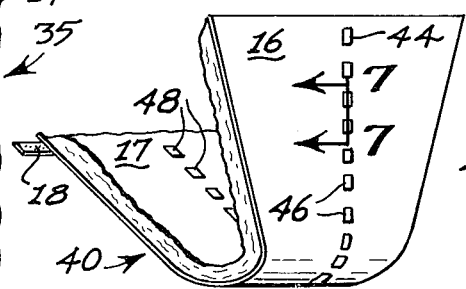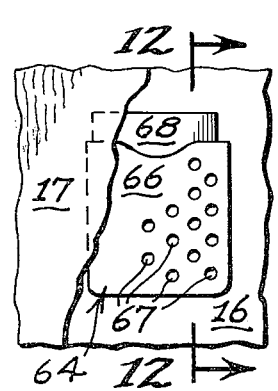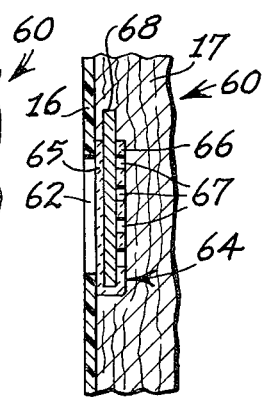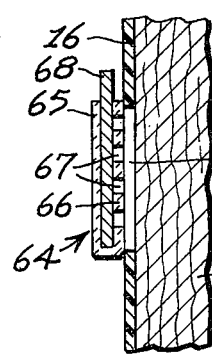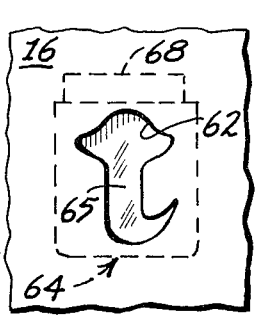

HUMIDITY INDICATING DIAPER COVER

BACKGROUND OF THE INVENTION

This invention relates to diapers or other sheet material, having moisture absorbent material, and more particularly to a humidity or moisture indicating diaper or similar moisture absorbing material.

The early detection of moisture within diapers is an important factor in maintaining sanitary and healthful conditions for babies and others who cannot control their elimination processes. This is especially true for persons having sensitive skin, particularly to acid within the urine.

Under normal conditions moisture within a standard disposable, or re-usable, diaper is not observed for a considerable length of time. It is usually necessary for a person to feel the inside of a diaper with his fingers to determine if moisture is present.

Moisture indicating devices for detection of moisture within diapers are well known in the art as illustrated in the Baker U.S. Pat. No. 3,675,654 and the Eidus U.S. Pat. No. 3,731,685. The Baker patent discloses finely divided water-soluble dye particles freely disposed between the outer transparent, water-impervious sheet material and the inner absorbent material. The Eidus indicator includes an elongated wicking strip fixed to a surface of the diaper and projecting laterally therefrom, with a moisture sensitive, color-changing agent on the projected end portion of the indicator strip.

SUMMARY OF THE INVENTION

It is an object of this invention to provide an improved humidity or moisture indicating structure for a diaper, having a moisture or liquid impervious outer sheet and a moisture absorbent inner sheet, by employing a moisture indicator strip which is in direct communication with the moisture absorbent inner sheet, immediately sensitive to the moisture and immediately visible exteriorly of the outer sheet, without an intermediate step of wicking.

One advantage of the diaper structure and indicator strip of this invention is that the strip may be incorporated in an existing diaper structure, or it may be incorporated in the original manufacture of the diaper.

The indicator strip utilized in this invention may be litmus paper, food coloring agent, or preferably what is known in the trade as "humidity indicator paper". The indicator paper or strip may be secured flat in a prominently visible area on the outer surface of the outer sheet of the diaper, which is provided with a hole or opening through the outer sheet so that any moisture is immediately communicated through the opening between the indicator strip and the moisture-laden absorbent inner sheet. Variations of this arrangement may be made by inserting a portion of the indicator strip through the opening so that it directly contacts the absorbent inner sheet. The indicator strip may be secured to the outer surface of the outer sheet by pressure-sensitive transparent tape, by adhesive material on the back of the strip adhering to the outer surface of the outer sheet, or by special mounting devices such as a pocket member having an external transparent wall and a perforated inner wall communicating with the hole through the outer sheet of the diaper.

In another form of the invention, the indicator strip may be mounted inside or behind the outer sheet, either between the outer sheet and the inner sheet, imbedded in the absorbent material of the inner sheet, or secured to the inner surface of the inner sheet. In this arrangement, a transparent opening is still formed through the outer sheet and as deep into the inner sheet as necessary so that the indicator strip is clearly visible through the hole or transparent opening from the outside of the outer sheet. A pocket having a transparent front wall and a perforated back wall may also be used to receive the indicator strip behind the outer sheet, so long as the transparent front wall is in registry with the opening through the outer sheet.

BRIEF DESCRIPTION OF THE DRAWINGS

FIG. 1 is a plan view of the inner face of one form of diaper structure made in accordance with this invention;

FIG. 2 is a front exterior view of the diaper disclosed in FIG. 1 fitted upon a person;

FIG. 3 is an enlarged fragmentary section taken along the line 3—3 of FIG. 1;

FIG. 4 is a section similar to FIG. 3 showing a first modification;

FIG. 5 is a fragmentary section similar to FIG. 3 disclosing a second modification;

FIG. 6 is a perspective view of a modified form of diaper construction;

FIG. 7 is an enlarged fragmentary section taken along the line 7—7 of FIG. 6;

FIG. 8 is a view similar to FIG. 3 disclosing another modification;

FIG. 9 is a view similar to FIG. 3 showing a further modification;

FIG. 10 is an enlarged fragmentary exterior view of another modified diaper construction;

FIG. 11 is a fragmentary interior view of the diaper disclosed in FIG. 10 with a portion of the inner sheet removed;

FIG. 12 is a fragmentary section taken along the line 12—12 of FIG. 11; and

FIG. 13 is a view similar to FIG. 12 disclosing a further modification.

DESCRIPTION OF THE PREFERRED EMBODIMENTS

Referring now to the drawings in more detail, FIGS. 1 – 3 disclose one modification of a diaper 15 made in accordance with this invention. The particular diaper 15 is constructed of an outer sheet 16 of any material substantially impervious to liquid, such as vinyl plastic, and an inner sheet of liquid or moisture absorbent material 17. As disclosed in FIG. 1, the diaper 15 may be provided with tabs 18 having pressure sensitive adhesive surfaces for securing the diaper 15 about the torso 19 of a person, such as a baby.

The diaper construction thus far described is well-known in the art.

In the diaper disclosed in FIGS. 1 – 3, a moisture indicator strip 20 is mounted flush against the exterior surface of the outer sheet 15 by any convenient mounting means, such as the transparent tape 21 having a pressure sensitive adhesive surface 22 for self-adhesion to the exterior surface of the outer sheet 16. Of course, the surface 22 may be of any other type of adhesive material, such as heat-sensitive adhesive material, or it may be a separate adhesive material, such as paste or glue, or even stitching.

Formed entirely through the thicknesses of both the outer sheet 16 and the inner sheet 17 is one or more holes or openings 24, two such holes being disclosed in FIGS. 1 and 3. These openings 24 are in registry or liquid communication with the inner surface of the moisture indicator strip 20, so that any liquid absorbed by the absorbent inner sheet 17 expresssed into the hole 24 may pass through the hole 24 until it is absorbed by the moisture indicator strip 20. The moisture indicator strip 20 may be a strip of paper, cloth or other fabric or sheet material which is made from, or impregnated with, a chemical agent adapted to change state when exposed and in contact with moisture or liquid, and particularly water. In the preferred form of the invention, the moisture indicator strip 20 is impregnated with a chemical agent capable of changing color so that the color change from moisture exposure is immediately visible through the transparent tape 21 from the outside of the diaper 15. Although litmus paper or paper impregnated with food coloring particles may be used, nevertheless commercially available "humidity indicator paper" is preferred.

The holes 24 disclosed in FIG. 3 may also be limited to projecting only through the outer sheet 16, so that the absorbent sheet 17 will normally lie in close proximity, if not continually touching the inner surface of the moisture indicator strip 20, so that the moisture indicator strip 20 is immediately sensitive to any moisture present in the absorbent inner sheet 17.

In the modified diaper construction 25 of FIg. 4, having the same moisture impervious outer sheet material 16 and an absorbent inner sheet 17, a single hole 34 is disclosed extending through only the outer sheet 16. The moisture indicator strip 20 has a first portion 26 held flush against the exterior surface of the outer sheet 16 by the plastic transparent tape 21. However, the upper portion 27 of the strip 20 extends through the opening 34 and upward behind the outer sheet 16 between the inner surface of the outer sheet 16 and the outer surface of the absorbent inner sheet 17. In this construction, there is a more intimate contact over a greater surface area between the upper portion 27 of the indicator strip 20 and the absorbent inner sheet 17, while the lower portion 26 of the indicator strip 20 is clearly exposed to view on the outer surface of the outer sheet 16 through the transparent tape 21.

The diaper construction 35 is FIG. 5 is identical to the diaper construction 25 in FIG. 4, with the exception that the lower portion 26 of the indicator strip 20 is mounted or secured flush against the exterior surface of the outer sheet 16 by a bonding material 36, such as glue, instead of the transparent adhesive tape 21.

FIGS. 6 and 7 disclose a diaper 40 having the outer sheet or cover 16 of moisture impervious material and the absorbent inner sheet 17. However, formed in longitudinally spaced arrangement are a plurality of holes or openings 42 through which are laced sinuously a very long indicator strip 44, which may otherwise be identical to the indicator strip 20. The outer portions 46 of the indicator strip 44 lie flush against the outer surface of the outer sheet 16 so that the portions 46 are clearly exposed to view for ready detection of any change in the indicator strip 44 created by exposure to moisture. The inner portions 48 lie flush between the inner surface of the outer sheet 16 and the outer surface of the inner sheet 17. Because of the multiple number of the inner portions 48 sandwiched between the inner and outer sheets 16 and 17, there is normally sufficient friction to eliminate the need of any adhesive material for bonding the indicator strip 44 in place.

Moreover, the longitudinally spaced inner portions 48, being in intimate contact with the moisture absorbent inner sheets 17 provide greater coverage, and therefore greater sensitivity to moisture conditions throughout the length of the inner liner or sheet 17 of the diaper 40.

In the modified diaper construction 50 of FIG. 8, a hole, or transparent opening 52, is formed only through the thickness of the impervious outer sheet 16. Sandwiched between the inner surface of the outer sheet 16 and the outer surface of the inner sheet 17 is the indicator strip 54 in registry with or spanning the transparent opening 52, so that at least a portion of the indicator strip 54 is clearly visible through the opening 52 from the outside of the diaper 50. The entire inner surface of the indicator strip 54 is in intimate contact with the absorbent material of the inner sheet or liner 17.

In FIG. 9, the diaper 55 is similar to the diaper 50 in FIG. 8 except the transparent opening 57 extends entirely through both thicknesses of the outer sheet 16 and the inner sheet 17, and the indicator strip 54 is secured by any adhesive or bonding material, such as glue 58 to the inner surface of the inner sheet 17, so that the middle portion of the indicator strip 54 is clearly visible through the hole 57 from the exterior of the diaper 55, while the peripheral portion of the indicator strip 54 is in intimate contact with the absorbent inner sheet 17.

The diaper construction 60 in FIGS. 10, 11 and 12, also includes a shaped, transparent opening 62 formed only through the thickness of the outer sheet 16. Spanning the opening 62 between the outer sheet 16 and the inner sheet 17 is a pocket member 64 having a transparent outer or front wall 65 and a perforated rear or inner wall 66 having a plurality of apertures 67 therethrough. Adapted to be received in the pocket formed between the front and rear walls 65 and 66 is an indicator member 68, which may be of identical composition and construction as the other indicator members such as 20. The front transparent wall 65 is adapted to span the opening 62 so that the indicator strip 68 received in the pocket member 64 is clearly visible through not only the transparent wall 65, but also the opening 62 from the exterior of the diaper 60. The outer face of the transparent wall 65 may be secured by adhesive, if desired, around the periphery of the opening 62 on the inner face of the outer sheet 16. The indicator strip 68 has maximum exposure to moisture within the absorbent inner sheet 17 because of its upper portion projecting above the top of the pocket member 64 and because of the moisture communication through the perforations 67 in the back wall 66.

The diaper construction 70 of FIG. 13 is similar to the diaper construction 60 of FIGS. 10 – 12, with the exception that the pocket member 64 receiving the indicator strip 68 is secured by any conventional adhesive means, not shown, to the outer surface of the outer sheet 16 spanning, and in registry with, the opening 62. In the diaper 70, the rear wall 66 is secured to the outer surface of the outer sheet 16 so that the apertures 67 are in liquid communication through the opening 62 with the inner sheet 17.

In the diaper construction 60 of FIGS. 10–12, the transparent opening 62 could be solid transparent material forming an integral part of the outer sheet 16. Of course, the entire outer sheet 16 could be transparent, thereby obviating the necessity of the transparent hole 62.

It is therefore believed that a humidity indicating diaper construction of various modifications has been illustrated in all of which modifications an indicator strip is utilized for almost immediate moisture indication. All of the indicator strips 20, 44, 54 and 68 are not only in immediate, if not intimate, contact with the absorbent material of the inner sheet for rapid sensitivity to the existence of moisture within the inner sheet 17, but are also immediately visible to an observer exterior of the respective diapers.

It will also be seen that most of the indicator strips, as well as the various openings, may be incorporated into existing diapers with a minimum of time and effort, as well as being incorporated in the originally manufactured diapers.

What is claimed is:
1. A humidity indicating diaper comprising:
   a. an outer sheet of material substantially impervious to liquid, having an outer face and an inner face,
   b. an inner sheet of liquid-absorbing material against the inner face of said outer sheet,
   c. a hole extending through said outer sheet from said outer face to said inner face and in liquid communication with said inner sheet,
   d. a moisture indicator strip of material impregnated with a chemical agent adapted to change state in the presence of moisture,
   e. means mounting at least a portion of said indicator strip on the outer face of said outer sheet so that said portion of said indicator strip is visible from the outer face of said outer sheet,
   f. said mounting means mounting at least a portion of said indicator strip in registry with said hole for communication with liquid through said hole.

2. The invention according to claim 1 in which said mounting means comprises a transparent tape covering said portion of said indicator strip on the outer face of said outer sheet, and means for securing said transparent tape upon the outer face of said outer sheet.

3. The invention according to claim 1 in which said entire indicator strip is mounted on said outer face.

4. The invention according to claim 1 in which a first portion of said indicator strip is mounted on said outer face and a second portion of said indicator strip extends through said opening.

5. The invention according to claim 4 in which said second portion of said indicator strip extends between the inner face of said outer sheet and said inner sheet.

6. The invention according to claim 5 comprising a plurality of said holes, said indicator strip being substantially elongated and sinuously threaded through said holes so that said first portions of said strip are mounted on said outer face and alternate with the second portions mounted on said inner face.

7. The invention according to claim 1 in which said mounting means comprises a pocket member having a transparent outer wall and a perforated inner wall, said perforated inner wall being fixed over and in liquid communication with said hole, said indicator strip being received in said pocket member between said inner and outer walls.

* * * * *